(12) United States Patent
Roth et al.

(10) Patent No.: US 9,504,593 B2
(45) Date of Patent: Nov. 29, 2016

(54) TOE PROTECTING CUSHION DEVICE

(71) Applicant: THE FEINSTEIN INSTITUTE FOR MEDICAL RESEARCH, Manhasset, NY (US)

(72) Inventors: Jesse Roth, Whitestone, NY (US); Gordon J. Berg, Glen Cove, NY (US)

(73) Assignee: The Feinstein Institute for Medical Research, Manhasset, NY (US)

(*) Notice: Subject to any disclaimer, the term of this patent is extended or adjusted under 35 U.S.C. 154(b) by 320 days.

(21) Appl. No.: 14/165,636

(22) Filed: Jan. 28, 2014

(65) Prior Publication Data

US 2014/0213954 A1    Jul. 31, 2014

Related U.S. Application Data

(60) Provisional application No. 61/757,766, filed on Jan. 29, 2013.

(51) Int. Cl.
*A61F 5/00* (2006.01)
*A61F 5/01* (2006.01)
*A61F 5/10* (2006.01)

(52) U.S. Cl.
CPC ............ *A61F 5/019* (2013.01); *A61F 5/0111* (2013.01); *A61F 5/10* (2013.01)

(58) Field of Classification Search
CPC .. A61F 5/0195; A61F 5/0111; A61F 5/0127; A61F 5/0585; A61F 13/04; A61F 2210/0085; A61F 5/019; A61F 5/05; A61F 2/4225; A61F 2202/30062; A61F 2002/30607; A61F 2002/30649; A61F 2002/30662; A61F 2013/00174; A61F 2013/00536; A61F 13/00008; A61F 13/00034; A61F 13/0006; A61F 13/00063; A61F 13/00068; A61F 13/041
USPC .................................... 602/30; 128/898–899
See application file for complete search history.

(56) References Cited

U.S. PATENT DOCUMENTS

| | | | | |
|---|---|---|---|---|
| 2,163,012 A | * | 6/1939 | Schenk | A61F 13/063 128/894 |
| 3,110,306 A | * | 11/1963 | Posner | A61F 5/019 128/894 |
| 3,211,142 A | * | 10/1965 | Johannes | A61F 5/019 602/30 |
| 7,131,939 B2 | * | 11/2006 | Ferri | A61F 5/10 132/75.6 |

* cited by examiner

*Primary Examiner* — Michael Brown
(74) *Attorney, Agent, or Firm* — Tarolli, Sundheim, Covell & Tummino LLP

(57) ABSTRACT

Toe cushioning device for protecting a patient's toes. A toe cushion device includes two tubular cushions positioned in a transverse plane on the plantar side of a patient's toes during use. The toe cushion relieves foot or toe pain and conforms to the changing contour of the patient's foot and toes during use.

34 Claims, 6 Drawing Sheets

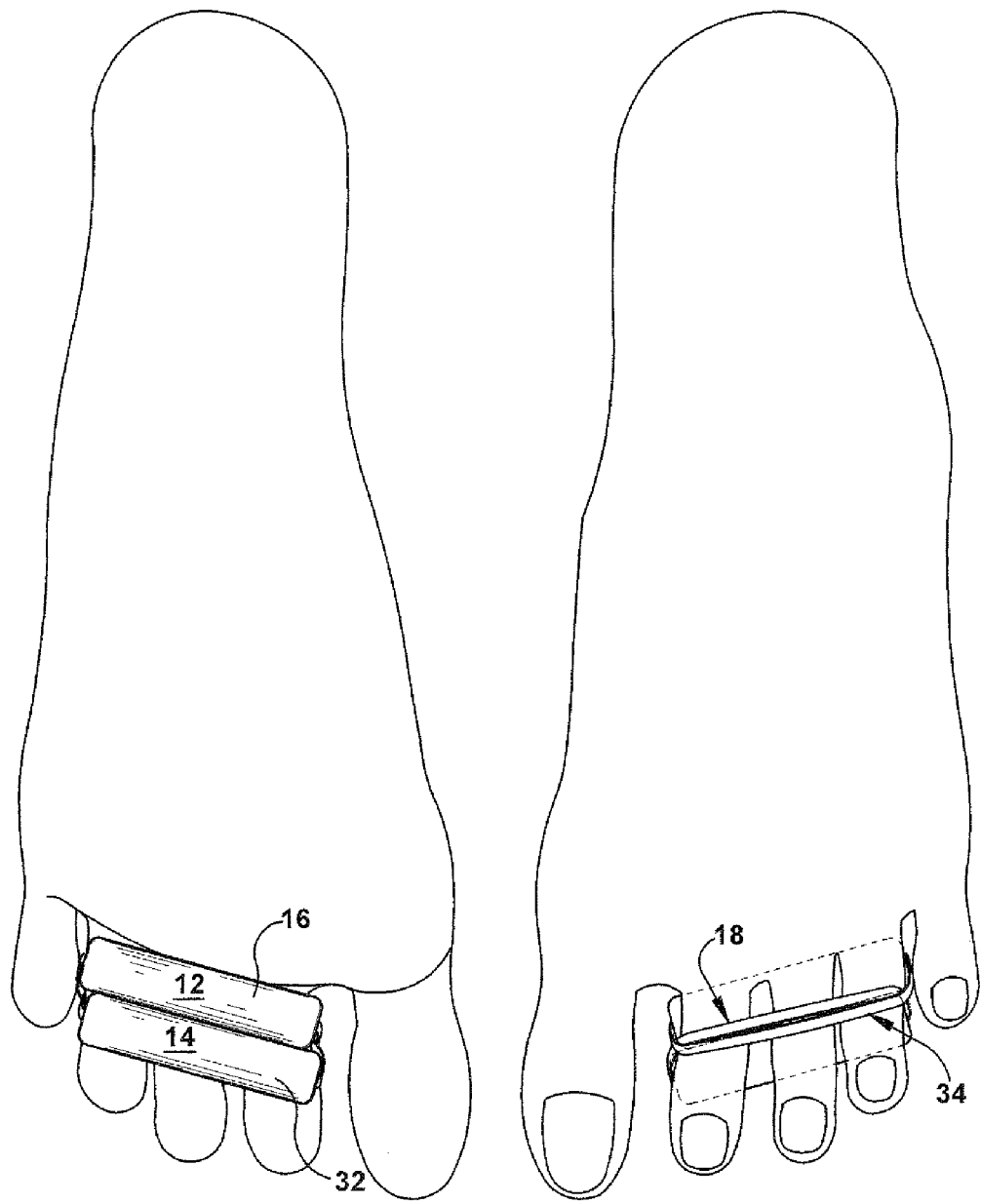

TOE PROTECTING CUSHION DEVICE

RELATED APPLICATION

This application claims priority from U.S. Provisional Application No. 61/757,766, filed 29 Jan. 2013, the subject matter of which is incorporated herein by reference in its entirety.

TECHNICAL FIELD

The present invention relates to devices for cushioning a patient's toes to relieve toe and distal foot pain.

BACKGROUND

Aging, diabetes, and other conditions lead to loss of joint flexibility in the foot and particularly in the toes. When such joint flexibility is lost, the pressure exerted against the feet while walking is mal-distributed, leading to excess pressure exerted on the planar side of the toes. This results in inflammation, pain and tissue damage. This condition is commonly referred to as "hammertoe."

The major shortcoming of currently available devices for treating hammertoe and other painful foot conditions is that the devices are fabricated from solid materials and therefore have a fixed structure. Even if these materials have been molded to the foot exactly, they still are inadequate because the foot changes contours continuously during the course of the day. Solid cushions may be useful for some part of the day but most other times fail or are ineffective because the foot changes contour. As such, a device is needed that continues to conform to the changing shape of the foot and toes providing continuous support.

SUMMARY OF THE INVENTION

The present invention relates to devices comprising a toe cushion that is positioned on the plantar side of a patient's toes. In an embodiment, the present invention provides a cushion device for protecting a patient's toes comprising a proximal member and a distal member. The proximal member comprises a plantar portion and a dorsal portion. The plantar portion has a front surface and a back surface. The plantar portion comprises a tubular cushion having a first end and a second end. The plantar portion is positioned in a transverse plane on a plantar side of the patient's toes in an operative configuration. The dorsal portion comprises a strap extending from the first end and second end of the tubular cushion and is secured against a dorsal side of the patient's toes in an operative configuration. The distal member also comprises a plantar portion and a dorsal portion. The plantar portion has a front surface and a back surface. The plantar portion comprises a tubular cushion having a first end and a second end. The plantar portion is positioned in a transverse plane on a plantar side of the patient's toes in an operative configuration of the distal member. The dorsal portion of the distal member comprises a strap extending from the first end and second end of the tubular cushion. In an operative configuration, the dorsal portion of the distal member is secured against a dorsal side of the patient's toes and the back surface of the distal member's plantar portion is contiguous with the front surface of the proximal member's plantar portion.

In another embodiment, the present invention provides a cushion device for protecting a patient's toes comprising a proximal member, a distal member, and a strap. The proximal member comprises a plantar portion that has a front surface and a back surface. The plantar portion comprises a tubular cushion having a first end and a second end. The plantar portion is positioned in a transverse plane on a plantar side of the patient's toes in an operative configuration of the proximal member. The distal member also comprises a plantar portion that has a front surface and a back surface. The plantar portion comprises a tubular cushion having a first end and a second end. The plantar portion of the distal member is positioned in a transverse plane on a plantar side of the patient's toes in an operative configuration of the distal member. The strap extends from the first and second ends of the tubular cushions of the proximal and distal members. In an operative configuration, the strap is secured against a dorsal side of the patient's toes and the back surface of the distal member's plantar portion is contiguous with the front surface of the proximal member's plantar portion.

In another embodiment, the present invention provides a cushion device for protecting a patient's toes. The cushion device comprises a proximal member and a distal member. The proximal member comprises a plantar portion having a front surface and a back surface. The proximal member also comprises a tubular cushion positioned in a transverse plane on a plantar side of the patient's toes in an operative configuration of the proximal member. The proximal member further comprises a hollow sleeve encasing the tubular cushion. At least of portion of the sleeve is secured to a dorsal side of the patient's toes in an operative configuration of the proximal member. The distal member also comprises a plantar portion having a front surface and a back surface. The distal member comprises a tubular cushion positioned in a transverse plane on a plantar side of the patient's toes in an operative configuration of the distal member. The distal member further comprises a hollow sleeve encasing the tubular cushion. In an operative configuration, a portion of the hollow sleeve is secured to a dorsal side of the patient's toes and the back surface of the distal member's plantar portion is contiguous with the front surface of the proximal member's plantar portion.

In another embodiment, the present invention provides a cushion device for protecting a patient's toes comprising a proximal member, a distal member, and a hollow sleeve. The proximal member comprises a plantar portion having a front surface and a back surface. The proximal member also comprises a tubular cushion positioned in a transverse plane on a plantar side of the patient's toes in an operative configuration of the proximal member. The distal member also comprises a plantar portion having a front surface and a back surface. The distal member comprises a tubular cushion positioned in a transverse plane on a plantar side of the patient's toes in an operative configuration of the distal member. The cushion device also comprises a hollow sleeve encasing the tubular cushions of the proximal member and the distal member. In an operative configuration, a portion of the hollow sleeve is secured to a dorsal side of the patient's toes and the back surface of the distal member's plantar portion is contiguous with the front surface of the proximal member's plantar portion.

BRIEF DESCRIPTION OF THE DRAWINGS

FIG. 3 is a plantar view of a plantar side of a patient's foot depicting the plantar portions of the cushion device of FIG. 1 in an operative configuration according to an embodiment of the present invention.

FIG. 4 is a dorsal view of the dorsal side of the foot illustrated in FIG. 3 depicting the dorsal portions of the device of FIG. 1.

DETAILED DESCRIPTION

The present invention provides toe cushion devices for protecting a patient's toes. In a preferred embodiment, the patient is a human being. The toe cushion devices can be used to redistribute pressure exerted against the patient's toes during walking or other foot movement. The toe cushion devices can be used to relieve pain, inflammation, joint deformity (including hammertoe), other painful conditions of the feet and toes, and/or for generally protecting the patient's toes. The toe cushion devices fit in the space under the toes. The toe cushion devices of the present invention can continue to change shape during the course of wearing to conform to the changing shape of the foot and toes providing continuous support. Specifically, during use as the day progresses, the toe cushion devices continuously "re-mold" and re-orient themselves in relation to each other in response to continuous changes in the shape of the foot. Weight bearing and walking molds the toe cushion devices to fit in the space between the foot and the inner sole of the patient's shoe (if the patient is wearing shoes).

Figure 1:
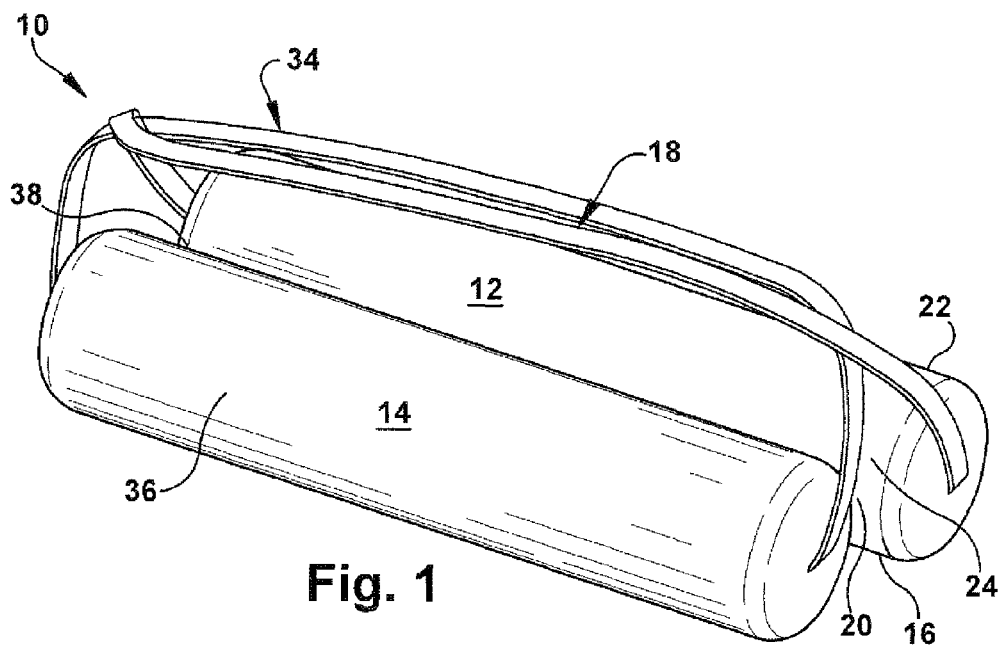
FIG. 1 is a perspective view of a cushion device according to an embodiment of the present invention.
Figure 2:
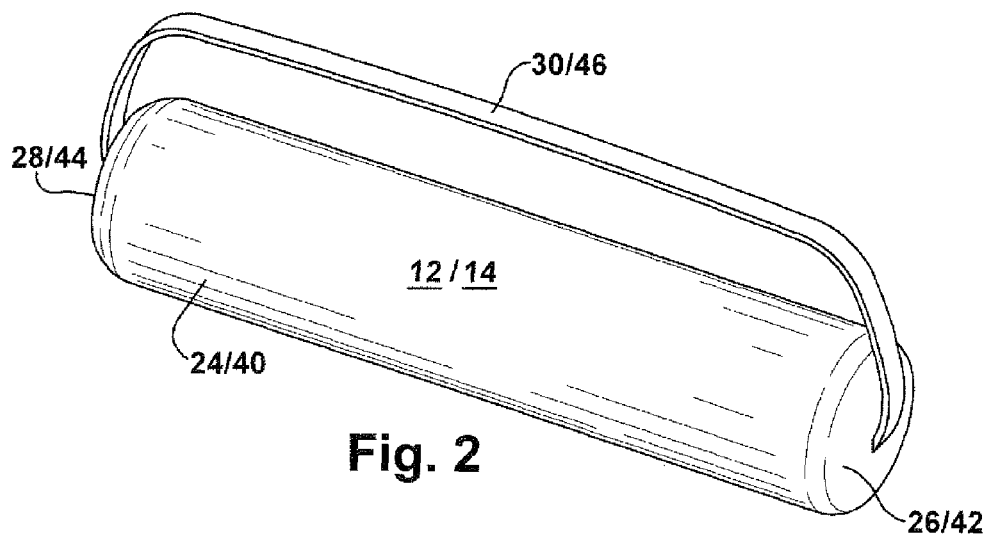
FIG. 2 is a perspective view of the proximal and/or distal member of the cushion device of FIG. 1 according to an embodiment of the present invention.

Referring to FIGS. 1 to 5, in an embodiment, a toe cushion device 10 comprises a proximal member 12 and a distal member 14. Proximal member 12 comprises a plantar portion 16 and a dorsal portion 18. Plantar portion 16 has a front surface 20 and a back surface 22. Plantar portion 16 comprises a tubular cushion 24 having a first end 26 and a second end 28 as shown in FIG. 2. In an operative configuration (when the patient is wearing the toe cushion device), plantar portion 16 is positioned in a transverse plane on a plantar side of the patient's toes as shown in FIG. 3. Dorsal portion 18 comprises strap 30 extending from first end 26 and second end 28 of tubular cushion 24 as shown in FIG. 2 and is secured against a dorsal side of the patient's toes in an operative configuration as shown in FIG. 4. Distal member 14 comprises plantar portion 32 and dorsal portion 34 as shown in FIGS. 3 and 4. Plantar portion 32 has front surface 36 and back surface 38 as shown in FIG. 1. Plantar portion 16 comprises a tubular cushion 40 having first end 42 and second end 44 as shown in FIG. 2. Plantar portion 32 is positioned in a transverse plane on a plantar side of the patient's toes in an operative configuration of distal member 14 as shown in FIG. 3. Dorsal portion 34 of distal member 14 comprises strap 46 extending from first end 42 and second end 44 of tubular cushion 40. As shown in FIGS. 3 and 4, in an operative configuration, dorsal portion 34 of distal member 14 is secured against a dorsal side of the patient's toes and back surface 38 of the distal member's plantar portion 32 is contiguous with front surface 20 of proximal member's plantar portion 16.

Figure 5:
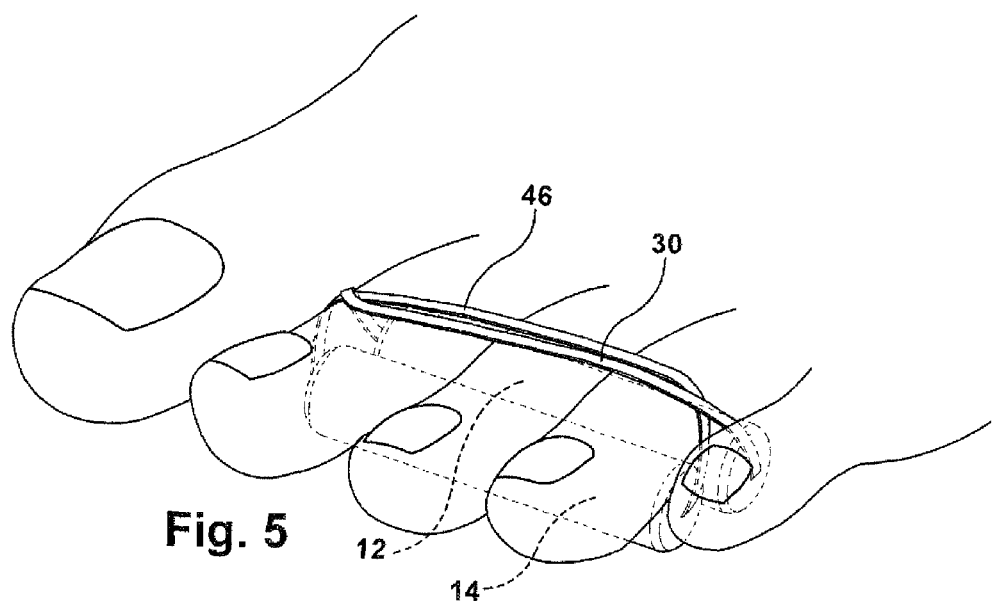
FIG. 5 is perspective view of a patient's toes with the device illustrated in FIG. 1 in an operative configuration.

As shown in FIG. 5, in an embodiment, the straps 30 and 46 of proximal member 12 and distal member 14 are intertwined to stabilize the toe cushion device in place. The straps can comprise free ends that are connected by a fastener on the dorsal side of the patient's toes in an operative configuration. Non-limiting examples of fasteners are adhesive tape, a suture, snap connection or any male/female connection system. The free ends can also be tied together instead of using a fastener.

In certain embodiments, the toe cushion device described above includes a hollow sleeve that covers the proximal member's toe cushion and a hollow sleeve that cover the distal member's toe cushion to protect the toe cushion. The sleeves can be disposed after usage.

Figure 6:
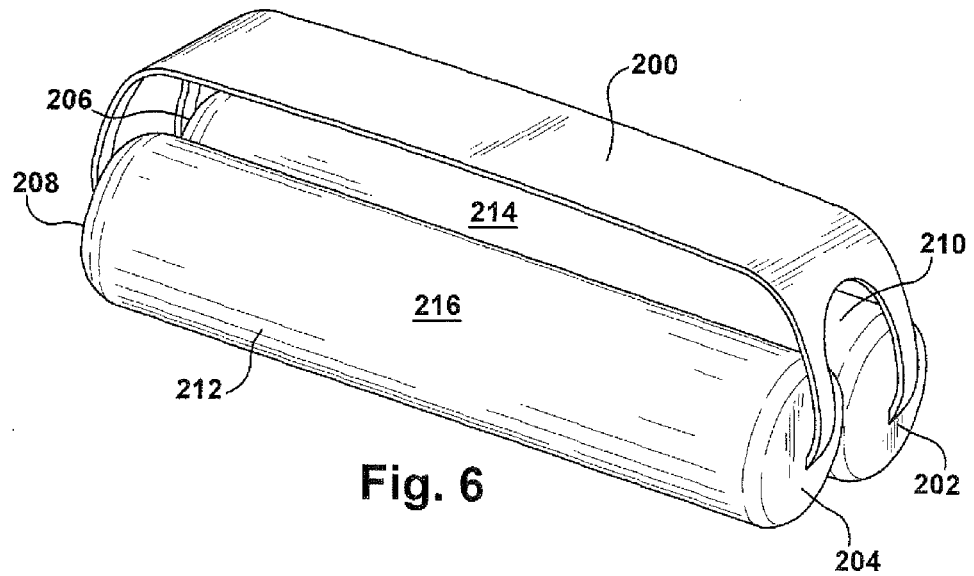
FIG. 6 is a perspective view of a cushion device according to an embodiment of the present invention.

Although the toe cushion device depicted in FIG. 1 comprises two separate straps, in an alternative embodiment as shown in FIG. 6, a toe cushion device can comprise a single strap 200 that extends from the first ends 202 and 204 and second ends 206 and 208 of the tubular cushions 210 and 212 of the respective proximal 214 and distal member 216.

Figure 7:
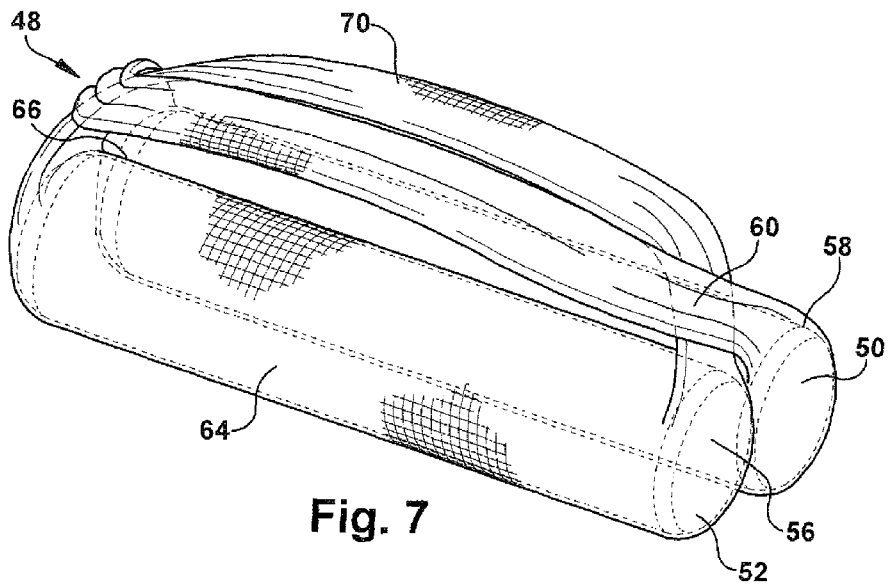
FIG. 7 is a perspective view of a cushion device according to an embodiment of the present invention.
Figure 8:
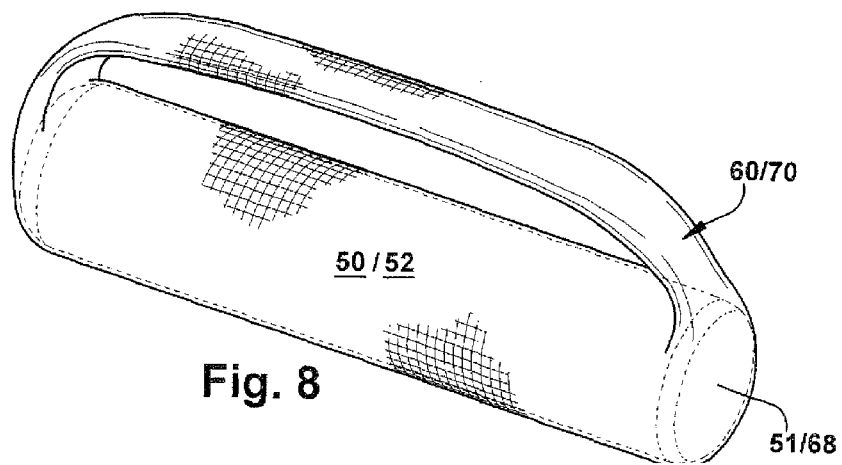
FIG. 8 is a perspective view of a proximal and/or distal member of the cushion device of FIG. 7 according to an embodiment of the present invention.
Figure 9:
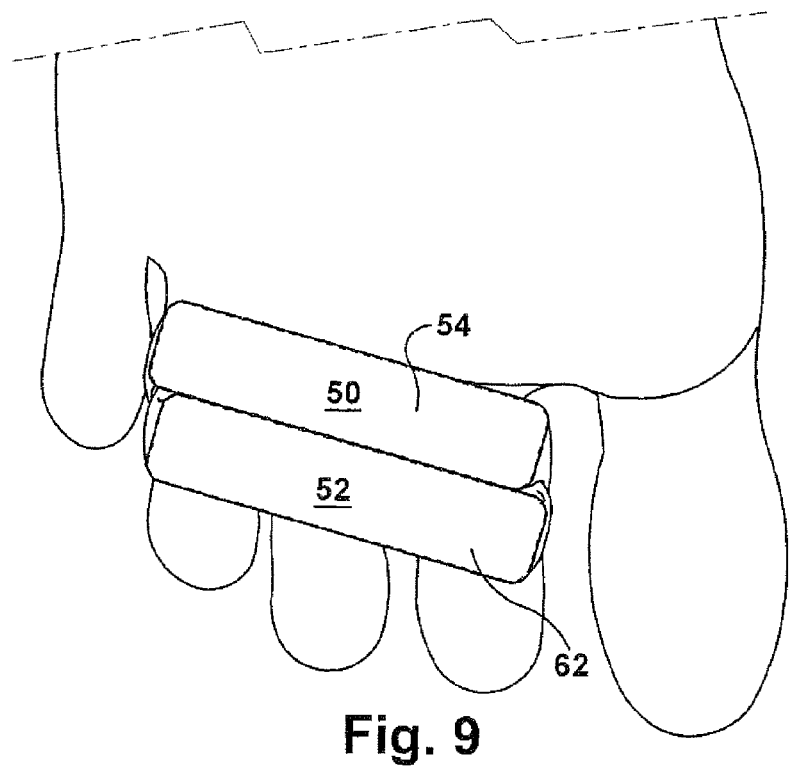
FIG. 9 is a plantar view of a plantar side of a patient's foot depicting the plantar portions of the cushion device of FIG. 7 in an operative configuration according to an embodiment of the present invention.
Figure 10:
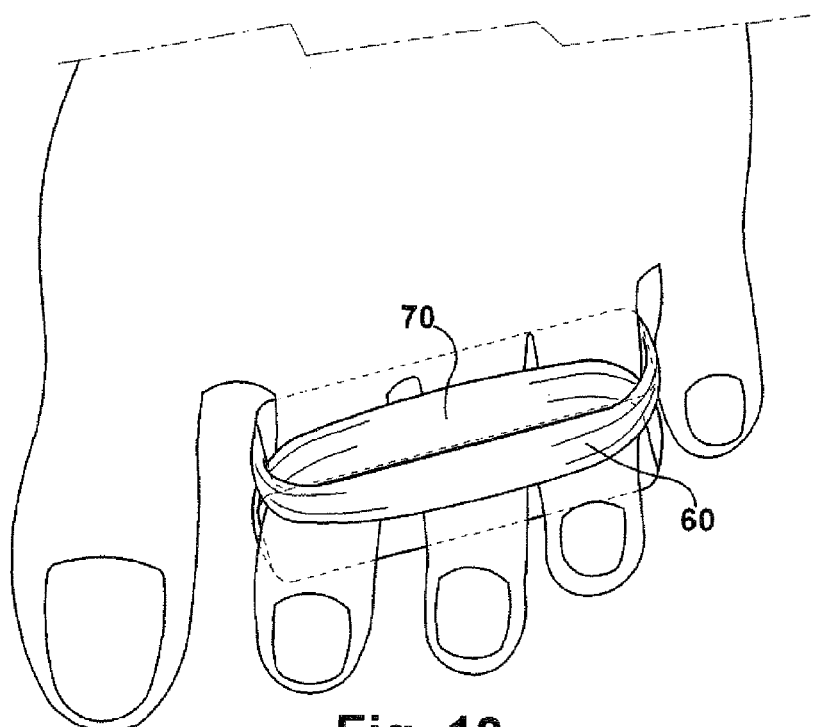
FIG. 10 is a dorsal view of the dorsal side of the foot illustrated in FIG. 9 depicting the dorsal portions of the device of FIG. 7.

Referring to FIGS. 7 to 10, in an embodiment, the present invention provides cushion device 48 comprises proximal member 50 and distal member 52. Proximal member 50 comprises plantar portion 54 as shown in FIG. 9. Plantar portion 54 has front surface 56 and back surface 58. Proximal member 50 also comprises tubular cushion 51 positioned in a transverse plane on a plantar side of the patient's toes in an operative configuration of proximal member 50 as shown in FIG. 9. Proximal member also comprises hollow sleeve 60 encasing tubular cushion 51 as shown in FIG. 8. As shown in FIG. 10, at least of portion of sleeve 60 is secured to a dorsal side of the patient's toes in an operative configuration of proximal member. Distal member 52 comprise plantar portion 62 having front surface 64 and back surface 66. Distal member 52 comprises tubular cushion 68 positioned in a transverse plane on a plantar side of the patient's toes in an operative configuration of distal member 52 as shown in FIG. 9. Distal member 52 also comprises hollow sleeve 70 encasing tubular cushion 68. As shown in FIGS. 9 and 10, in an operative configuration, a portion of hollow sleeve 70 is secured to a dorsal side of the patient's toes and back surface 66 of distal member's plantar portion 62 is contiguous with front surface 56 of the proximal member's plantar portion 54.

In certain embodiments, the hollow sleeve of proximal member and the hollow sleeve of the distal member each have free ends that are connected by a fastener on the dorsal side of the patient's toes in an operative configuration. Non-limiting examples of fasteners are adhesive tape, a suture, snap connection or any male/female connection system. The free ends can also be tied together instead of using a fastener. As shown in FIG. 10, the portion of hollow sleeves 60 and 70 that are secured to the dorsal side of the patient's toes can be intertwined to stabilize the toe cushion device in place.

Figure 11:
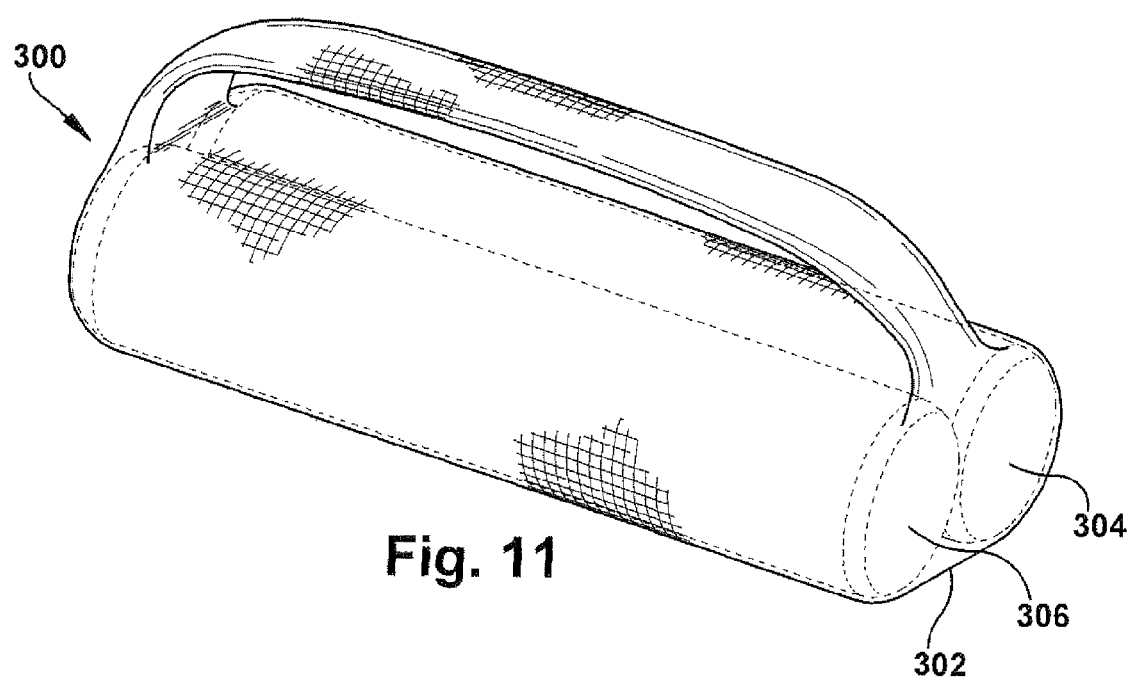
FIG. 11 is a perspective view of a cushion device according to an embodiment of the present invention.

Although the toe cushion device depicted in FIG. 7 comprises two separate hollow sleeves, in an alternative embodiment depicted in FIG. 11, a toe cushion device 300 comprises a single hollow sleeve 302 that encases both the proximal member 304 and the distal member 306. In either embodiment, the hollow sleeve(s) can be disposed after usage.

In preferred embodiments of the present invention, the tubular cushions of the proximal member and distal member of a toe cushion device are positioned on only the middle three toes of the patient during use. However, the tubular cushions can be positioned on more or less than the middle three toes of the patient depending on the patient's needs.

In certain embodiments, the proximal and distal members of a toe cushion device have different dimensions. For example, the proximal and distal members can have different lengths or diameters. For example, the proximal member can be shorter than the distal member or the distal member can be shorter than the proximal member. The tubular cushions can also have the same dimensions and be altered (e.g. cut) by the user or a physician to accommodate the particular patient's needs and foot structure.

The tubular cushion of the toe cushion devices described above is fabricated from a material that allows the tubular cushion to conform to the changing shape of the patient's foot and toes during use and return to its un-deformed shape between uses. Non-limiting examples of such materials include polyfoam, polyethylene and shape memory foam. The tubular cushion can comprise a spongy material or a gel material.

In preferred embodiments where the toe cushion device includes a hollow sleeve, the hollow sleeve comprises a woven fabric material. Also, in preferred embodiments, the hollow sleeve is fabricated from a stretchable material.

In a preferred embodiment, a toe cushion device as described above forms an elliptical ring around the patient's toes in an operative configuration. Further, a toe cushion device can be used on only a single foot of the patient or two separate toe cushions can be used on each foot of the patient.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What claimed is:

1. A cushion device for protecting a patient s toes comprising:
    a proximal member comprising:
        a plantar portion having a front surface and a back surface, the plantar portion comprising a tubular cushion having a first end and a second end, the plantar portion positioned in a transverse plane on a plantar side of the patient s toes in an operative configuration of the proximal member; and
        a dorsal portion comprising a strap extending from the first end and second end of the tubular cushion and secured against a dorsal side of the patient's toes in an operative configuration of the proximal member; and
    a distal member comprising:
        a plantar portion having a front surface and a back surface, the plantar portion comprising a tubular cushion having a first end and a second end, the plantar portion positioned in a transverse plane on a plantar side of the patient's toes in an operative configuration of the distal member; and
        a dorsal portion comprising a strap extending from the first end and second end of the tubular cushion, wherein in an operative configuration, the dorsal portion is secured against a dorsal side of the patient's toes and the back surface of the distal member's plantar portion is contiguous with the front surface of the proximal member's plantar portion.

2. The cushion device of claim 1, wherein the strap of the proximal member and the strap of the distal member are intertwined.

3. The cushion device of claim 1, further comprising a hollow sleeve covering the proximal member s toe cushion and a hollow sleeve covering the distal member's toe cushion.

4. The cushion device of claim 3, wherein the sleeve of the proximal member and the sleeve of the distal member are disposable.

5. The cushion device of claim 1, wherein in an operative configuration, the tubular cushion of the proximal member and tubular cushion of the distal member are positioned on only the middle three toes of the patient.

6. The cushion device of claim 1, wherein the toe cushion of the proximal member has a different length and/or diameter than the toe cushion of the distal member.

7. The cushion device of claim 1, wherein the toe cushion of the proximal member and the toe cushion of the distal member comprise a polyfoam material, a polyethylene material, or a shape memory foam material.

8. The cushion device of claim 1, wherein the proximal member and the distal member each form an elliptical ring around the patient's toes in an operative configuration.

9. A cushion device for protecting a patient s toes comprising:
    a proximal member comprising a plantar portion having a front surface and a back surface, the plantar portion comprising a tubular cushion having a first end and a second end, the plantar portion positioned in a transverse plane on a plantar side of the patient's toes in an operative configuration of the proximal member; and
    a distal member comprising: a plantar portion having a front surface and a back surface, the plantar portion comprising a tubular cushion having a first end and a second end, the plantar portion positioned in a transverse plane on a plantar side of the patient's toes in an operative configuration of the distal member; and a strap extending from the first and second ends of the tubular cushions of the proximal and distal members, wherein in an operative configuration, the strap is secured against a dorsal side of the patient's toes and the back surface of the distal member's plantar portion is contiguous with the front surface of the proximal member's plantar portion.

10. The cushion device of claim 9, further comprising a hollow sleeve covering the proximal member's toe cushion and a hollow sleeve covering the distal member's toe cushion.

11. The cushion device of claim 10, wherein the sleeve of the proximal member and the sleeve of the distal member are disposable.

12. The cushion device of claim 9, wherein in an operative configuration, the tubular cushion of the proximal member and the tubular cushion of the distal member are positioned on only the middle three toes of the patient.

13. The cushion device of claim 9, wherein the toe cushion of the proximal member has a different length and/or diameter than the toe cushion of the distal member.

14. The cushion device of claim 9, wherein the toe cushion of the proximal member and the toe cushion of the distal member comprise a polyfoam material, a polyethylene material, or a shape memory foam material.

15. The cushion device of claim 9, wherein the proximal member and the distal member each form an elliptical ring around the patient's toes in an operative configuration.

16. A cushion device for protecting a patient's toes comprising:
  a proximal member comprising a plantar portion having a front surface and a back surface, the proximal member comprising a tubular cushion positioned in a transverse plane on a plantar side of the patient's toes in an operative configuration of the proximal member; and
  a hollow sleeve encasing the tubular cushion and at least of portion thereof secured to a dorsal side of the patient's toes in an operative configuration of the proximal member; and
  a distal member comprising a plantar portion having a front surface and a back surface, the distal member comprising: a tubular cushion positioned in a transverse plane on a plantar side of the patient's toes in an operative configuration of the distal member; and a hollow sleeve encasing the tubular cushion, wherein in an operative configuration, a portion of the hollow sleeve is secured to a dorsal side of the patient's toes and the back surface of the distal member's plantar portion is contiguous with the front surface of the proximal member's plantar portion.

17. The cushion device of claim 16, wherein the sleeve of the proximal member and the sleeve of the distal member each have a first end and a second end connected by a fastener on the dorsal side of the patient's toes in an operative configuration.

18. The cushion device of claim 16, wherein the sleeve of the proximal member and the sleeve of the distal member comprise a woven fabric material.

19. The cushion device of claim 16, wherein the sleeve of the proximal member and the sleeve of the distal member comprise a stretchable material.

20. The cushion device of claim 16, wherein the sleeve of the proximal member and the sleeve of the distal member are disposable.

21. The cushion device of claim 16, wherein in an operative configuration, the tubular cushion of the proximal member and tubular cushion of the distal member are positioned on only the middle three toes of the patient.

22. The cushion device of claim 16, wherein the toe cushion of the proximal member has a different length and/or diameter than the toe cushion of the distal member.

23. The cushion device of claim 16, wherein the toe cushion of the proximal member and the toe cushion of the distal member comprise a polyfoam material, a polyethylene material, or a shape memory foam material.

24. The cushion device of claim 1, wherein the proximal member and the distal member each form an elliptical ring around the patient's toes in an operative configuration.

25. A cushion device for protecting a patient's toes comprising:
  a proximal member comprising a plantar portion having a front surface and a back surface, the proximal member comprising: a tubular cushion positioned in a transverse plane on a plantar side of the patient's toes in an operative configuration of the proximal member; and
  a distal member comprising a plantar portion having a front surface and a back surface, the distal member comprising: a tubular cushion positioned in a transverse plane on a plantar side of the patient's toes in an operative configuration of the distal member; and
  a hollow sleeve encasing the tubular cushions of the proximal member and the distal member, wherein in an operative configuration, a portion of the hollow sleeve is secured to a dorsal side of the patient's toes and the back surface of the distal member's plantar portion is contiguous with the front surface of the proximal member's plantar portion.

26. The cushion device of claim 25, wherein the sleeve has a first end and a second end connected by a fastener on the dorsal side of the patient's toes in an operative configuration.

27. The cushion device of claim 25, wherein the sleeve of the proximal member and the sleeve of the distal member comprise a woven fabric material.

28. The cushion device of claim 25, wherein the sleeve of the proximal member and the sleeve of the distal member comprise a stretchable material.

29. The cushion device of claim 25, wherein the sleeve of the proximal member and the sleeve of the distal member are disposable.

30. The cushion device of claim 25, wherein in an operative configuration, the tubular cushion of the proximal member and the tubular cushion of the distal member are positioned on only the middle three toes of the patient.

31. The cushion device of claim 25, wherein the toe cushion of the proximal member has a different length and/or diameter than the toe cushion of the distal member.

32. The cushion device of claim 25, wherein the toe cushion of the proximal member and the toe cushion of the distal member comprise a polyfoam material, a polyethylene material, or a shape memory foam material.

33. The cushion device of claim 25, wherein the proximal member and the distal member each form an elliptical ring around the patient's toes in an operative configuration.

34. A cushion device for protecting a patient's toes comprising:
  a proximal member comprising:
    a plantar portion having a front surface and a back surface, the plantar portion comprising a tubular cushion having a first end and a second end, the plantar portion positioned in a transverse plane on a plantar side of the patient's toes in an operative configuration of the proximal member; and
  a distal member comprising:
    a plantar portion having a front surface and a back surface, the plantar portion comprising a tubular cushion having a first end and a second end, the plantar portion positioned in a transverse plane on a plantar side of the patient's toes in an operative configuration of the distal member; and
  a strap connecting the first end and second end of the tubular cushions and secured against a dorsal side of the patient s toes in an operative configuration.

* * * * *

UNITED STATES PATENT AND TRADEMARK OFFICE
CERTIFICATE OF CORRECTION

PATENT NO.         : 9,504,593 B2
APPLICATION NO.    : 14/165636
DATED              : November 29, 2016
INVENTOR(S)        : Jesse Roth et al.

Page 1 of 1

It is certified that error appears in the above-identified patent and that said Letters Patent is hereby corrected as shown below:

In the Claims
Column 5, Line 57 reads "a patient s toes" should read --a patient's toes--
Column 5, Line 64 reads "the patient s toes" should read --the patient's toes--
Column 6, Line 22 reads "proximal member s toes" should read --proximal member's toes--
Column 6, Line 42 reads "a patient s toes" should read --a patient's toes--
Column 8, Line 65 reads "the patient s toes" should read --the patient's toes--

Signed and Sealed this
Twenty-fourth Day of January, 2017

Michelle K. Lee
*Director of the United States Patent and Trademark Office*